United States Patent [19]

Durette

[11] Patent Number: 5,236,899

[45] Date of Patent: * Aug. 17, 1993

[54] 6-POSITION CYCLOSPORIN A ANALOGS AS MODIFIERS OF CYTOTOXIC DRUG RESISTANCE

[75] Inventor: Philippe L. Durette, New Providence, N.J.

[73] Assignee: Merck & Co., Inc., Rahway, N.J.

[*] Notice: The portion of the term of this patent subsequent to Apr. 3, 2007 has been disclaimed.

[21] Appl. No.: 752,169

[22] Filed: Aug. 23, 1991

Related U.S. Application Data

[63] Continuation of Ser. No. 425,262, Oct. 23, 1989, abandoned, which is a continuation-in-part of Ser. No. 121,827, Nov. 16, 1987, Pat. No. 4,914,188.

[51] Int. Cl.$^5$ .................... A61K 37/02; C07K 7/64
[52] U.S. Cl. ........................ 514/11; 514/885; 514/908; 514/922; 514/970; 530/321
[58] Field of Search .............. 530/317, 321; 514/9, 514/11, 885, 908, 922, 970

[56] References Cited

U.S. PATENT DOCUMENTS

| | | | |
|---|---|---|---|
| 4,108,985 | 8/1978 | Ruegger et al. | 530/321 |
| 4,117,118 | 9/1978 | Harri et al. | 530/321 |
| 4,210,581 | 7/1980 | Ruegger et al. | 530/321 |
| 4,220,641 | 9/1980 | Traber et al. | 530/317 |
| 4,288,431 | 9/1981 | Traber et al. | 530/321 |
| 4,289,851 | 9/1981 | Traber et al. | 530/321 |
| 4,384,996 | 5/1983 | Bollinger et al. | 530/321 |
| 4,396,542 | 8/1983 | Wenger | 530/321 |
| 4,639,434 | 1/1987 | Wenger et al. | 514/11 |
| 4,681,754 | 7/1987 | Sigel | 514/11 |
| 4,703,033 | 10/1987 | Seebach | 514/11 |
| 4,914,188 | 4/1990 | Dumont et al. | 530/321 |

FOREIGN PATENT DOCUMENTS

0296122A2 12/1988 European Pat. Off. .

OTHER PUBLICATIONS

Suffness et al., J. Natural Products, vol. 45, pp. 1-14, (1982).
L. Slater, et al. Proc. Am. Assoc. Cancer Res. vol. 27 p. 392 (1986).
Wenger, R., Total Synthesis-Change in Molecular Structure-Biological Effect: Cyclosporin as Example, 1984/111 pp. 4-11.
Kobel and Traber, Directed Biosynthesis of Cyclosporins, 14 pp. 237-240 (1982).
Slater, et al., Cyclosporin A 27 p. 392 (1986).
Twentyman, et al., Cyclosporin A and its Analogues as Modifiers, 56 pp. 55-57 (1987).
Osieka, et al., Enhancement of Etoposide Induced Cytoxicity by Cyclosporin A, 18 pp. 198-202 (1986).
Nooter, et al. Effect of Cyclosporin A, 23 pp. 296-300 (1989).
Twentyman, Modification of Cytotoxic Drug Resistance, 57 pp. 254-258 (1988).
Twentyman, A Possible Role for Cyclosporins in Cancer Chemo. Anticancer Research, 8, pp. 985-994, (1988).

*Primary Examiner*—Y. Christina Chan
*Attorney, Agent, or Firm*—Curtis C. Panzer; Raymond M. Speer

[57] ABSTRACT

Cyclosporin analogs containing a MeAla or MeAbu residue at the 6-position of the cyclic undecapeptide have been discovered to sensitize multidrug resistant cells to certain chemotherapeutic agents. These cyclosporin analogs have also been shown to increase the sensitivity of cells already susceptible to the chemotherapeutic agents. In addition, these cyclosporin A analogs lack the nephrotoxic and immunosuppressive activity of cyclosporin A.

8 Claims, No Drawings

6-POSITION CYCLOSPORIN A ANALOGS AS MODIFIERS OF CYTOTOXIC DRUG RESISTANCE

RELATED APPLICATION

This application is a continuation of U.S. Ser. No. 425,262, filed Oct. 23, 1989 (now abandoned), which is a continuation-in-part of U.S. Ser. No. 121,827, filed Nov. 16, 1987 (now U.S. Pat. No. 4,914,188, issued Apr. 3, 1990).

BACKGROUND OF THE INVENTION

A major problem in the treatment of cancer is the emergence of tumor cell resistance to chemotherapeutic agents and the subsequent patient relapse. These cancer victims may fail to respond to any antitumor agent since these tumor cells tend to exhibit clinical resistance to many drugs. This phenomenon is termed multidrug-resistance (MDR). MDR is associated with certain alterations in tumor cells, including an over-expression of a certain high molecular weight membrane glycoprotein and a decrease in the ability of the tumor cell to accumulate and retain chemotherapeutic agents.

Drugs of proven antitumor chemotherapeutic value to which multidrug-resistance has been observed include vinblastine, vincristine, etoposide, teniposide, doxorubicin (adriamycin), daunorubicin, plicamycin (mithramycin) and actinomycin D. Many tumors are intrinsically multidrug-resistant (e.g. adenocarcinomas of the colon and kidney) while other tumors acquire multidrug-resistance during therapy (e.g. neuroblastomas and childhood leukemias).

Agents are available which can restore drug sensitivity to some MDR tumor cells. Among these agents known to possess this property are calcium transport blockers (e.g. verapamil) and calmodulin inhibitors (e.g. trifluoperazine). Clinical use of these compounds has been limited by their extremely toxic side effects [Twentyman, P. R. et al., Int. J. Radiat. Oncol. Biol. Phys. 12: 1355 (1986)].

Cyclosporin A (CsA), a member of the family of immunosuppressive cyclosporins, has also been shown to have the ability to reverse the resistance of tumor cells to certain antitumor chemotherapeutic agents, both in vitro and in vivo [Slater, L. et al., Proc. Am. Assoc. Cancer Res. 27, 392 (1982)]. The mechanism by which cyclosporin A modulates multidrug-resistance is not understood. However, during clinical trials, significant benefit has been observed when cyclosporin A was used in conjunction with antitumor chemotherapeutic agents in treating patients with multidrug-resistant tumors. Due to the success of cyclosporin A in sensitizing multidrug-resistant tumor cells, it is expected that the administration of cyclosporin A prior to the emergence of multidrug-resistant tumor cells would prevent their subsequent emergence. Generally, cyclosporins are not directly cytotoxic or myelotoxic.

Unfortunately, immunosuppressive cyclosporins, including CsA, are highly nephrotoxic. In addition to its nephrotoxicity, CsA is known to have the following additional negative side effects:

1) abnormal liver function;
2) hirsutism;
3) gum hypertrophy;
4) tremor;
5) hyperaesthesia;
6) gastrointestinal discomfort;
7) neurotoxicity; and
8) hypertension.

It is extremely undesirable to further compromise the health of a cancer victim by administering additional toxic drugs.

CsA is the drug of choice for preventing organ transplant rejection, and is also beneficial in treating autoimmune diseases, such as type 1 diabetes, multiple sclerosis, uveitis and rheumatoid arthritis. Despite these advantages, broader clinical application of CsA has been hampered by its severe nephrotoxicity (as well as other major organ toxicity) within the standard dose range of between 5 mg and 20 mg per kilogram per day.

The cyclosporins are a family of immunosuppressive compounds isolated from fermentation broths of various fungal species, including *Tolypocladium inflatum* and *Cylindrocarpon lucidum*.

The generic structure of the class of cyclosporins has been established as a cyclic peptide of formula I which contains 11 amino acids.

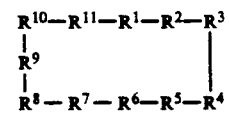

For example, cyclosporin A of formula II contains seven N-methylated amino acids and a novel "C-9 amino acid" at position 1, designated as (4R)-4-[(E)-2-butenyl]-4,N-dimethyl-L-threonine(MeBmt). This novel amino acid is located in what is referred to as position 1 and has been found to be crucial for the immunosuppressive activity of cyclosporin A.

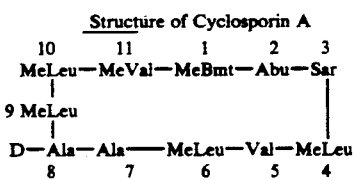

Unless specified, the amino acid configuration is L.

The present invention describes a use for cyclosporin analogs that are effective in increasing the sensitivity of tumor cells resistant to anticancer chemotherapeutic agents, such as doxorubicin (DOX). This class of cyclosporin analogs is obtained by substituting the MeLeu residue at the 6-position of CsA with a MeAla or MeAbu residue. As evaluated in an in vivo mouse model, the cyclosporin analogs of this invention did not exhibit any nephrotoxicity. Furthermore, these compounds are non-immunosuppressive. The compounds described herein are also capable of enhancing the sensitivity of multidrug-resistant cells and, given their lack of nephrotoxicity, as measured in an in vivo mouse model, are expected to find broader clinical application than cyclosporin A itself. These compounds have the effect, as described herein, of reducing the resistance of MDR tumor cells, and potentiating the sensitivity of cells susceptible to antitumor agents such as DOX. Furthermore, since these cyclosporin analogs maintain the MDR-modulatory properties of cyclosporin A, it is expected that they possess all other MDR-related benefits of cyclosporin A treatment. Given their lack of nephrotoxicity these compounds are expected to have broad clinical application and may play a significant role in fighting cancer.

OBJECTS OF THE INVENTION

An object of the present invention is to provide a method of sensitizing multidrug-resistant tumor cells using cyclosporin analogs containing a 6-MeAla or a 6-MeAbu residue. Another object of the present invention is to provide a method for increasing the sensitivity of tumor cells which are susceptible to certain antitumor agents using cyclosporin analogs containing a 6-MeAla or 6-MeAbu residue.

A further object of the present invention is to provide a method for treating MDR or drug sensitive tumor cells by administering prior to, together with, subsequent to, or in combination with an antitumor chemotherapeutic agent, a sufficient amount of one or both of the 6-MeAla or 6-MeAbu cyclosporin analogs.

An additional object of the present invention is to provide a method of treating MDR or drug-sensitive tumor cells with one or both of the 6-MeAla or 6-MeAbu cyclosporin analogs without nephrotoxic side effects associated with cyclosporin A.

These and other objects of this invention will be apparent from the following description.

SUMMARY OF THE INVENTION

It has been discovered that the cyclosporin analogs 6-MeAla and 6-MeAbu have the ability to sensitize multidrug resistant tumor cells to antitumor chemotherapeutic agents, such as doxorubicin. It has also been discovered that these compounds have the ability to potentiate the sensitivity of tumor cells susceptible to these antitumor chemotherapeutic agents. In addition, in vivo studies have shown that these cyclosporin analogs lack the nephrotoxic side effects of cyclosporins and are non-immunosuppressive. Due to these properties, the 6-MeAla and 6-MeAbu compounds are expected to have broad clinical application and major significance.

DETAILED DESCRIPTION OF THE INVENTION

This invention relates to 6-position cyclosporin analogs of formula I

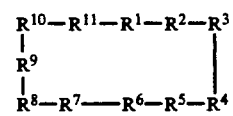

wherein:

$R^1$ is MeBmt;
$R^2$ is Abu;
$R^3$ is Sar;
$R^4$, $R^9$ and $R^{10}$ are MeLeu;

$R^5$ is Val;
$R^6$ is MeAla;
$R^7$ is Ala;
$R^8$ is D—Ala; and
$R^{11}$ is MeVal;

and wherein:

$R^1$ is MeBmt;
$R^2$ is Abu;
$R^3$ is Sar;
$R^4$ $R^9$ and $R^{10}$ are MeLeu;

$R^5$ is Val;
$R^6$ is MeAbu;
$R^7$ is Ala;
$R^8$ is D—Ala; and
$R^{11}$ is MeVal;

The 6-position cyclosporin analogs of this invention were prepared via cyclization of appropriate linear undecapeptides following well-established procedures which were slightly modified for better results. The procedure most used is published by R. W. Wenger et al. in *Helv. Chim. Acta*, 67, 502(1984).

The following scheme illustrates the application of this procedure to the synthesis of 6-position cyclosporin analogs of this invention.

Starting materials used in the process described in Scheme I are either known or available commercially or are prepared by the following procedures:

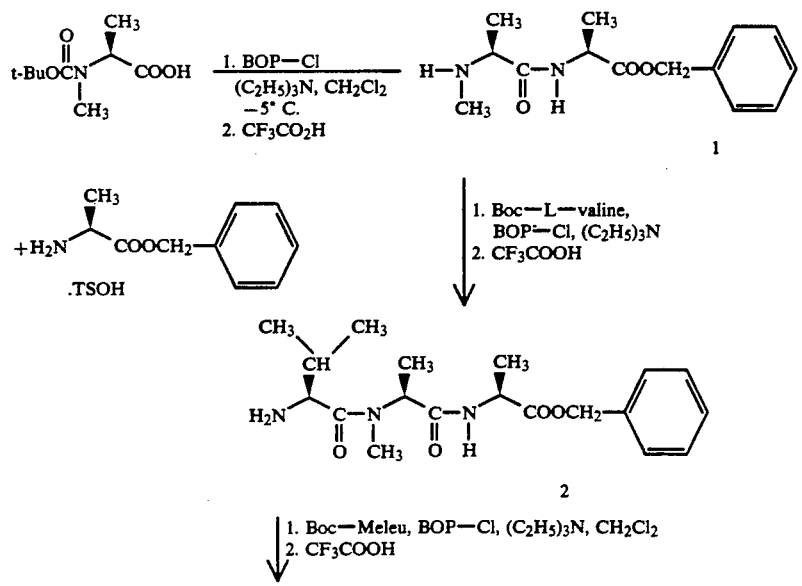

-continued

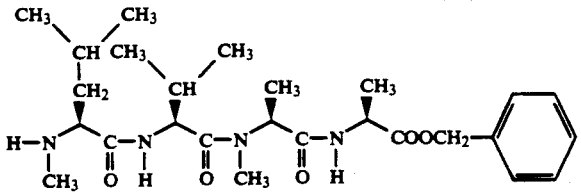

MeLeu   Val    MeAla   Ala

↓ 1. Boc—Abu—SarOH (4), BOP—Cl, (C₂H₅)₃N, CH₂Cl₂
  2. CF₃COOH

H—Abu—Sar—MeLeu—Val—MeAla—Ala—OBzl
(wherein OBzl represents OCH₂phenyl)

5

↓ 1. N, O-Isopropylidene-MeBnt,
     N-methylmorpholine, BtOH, DCC, THF
  2. H⁺

H—MeBnt—Abu—Sar—MeLeu—Val—MeAla—Ala  OBzl

6

↓ Boc—D—Ala—MeLeu—MeLeu—MeValOH,
  BOP, CH₂Cl₂, N-methylmorpholine

Boc—D—Ala—MeLeu—MeLeu—MeVal—MeBnt—Abu—Sar—MeLeu
                                              |
                   Benzyl—O—Ala—MeAla—Val

7

↓ 1. OH⁻
  2. CF₃COOH

H—D—Ala—MeLeu—MeLeu—MeVal—MeBnt—Abu—Sar—MeLeu
                                              |
                       HO—Ala—MeAla—Val

8

↓ cyclization

MeLeu—MeVal—MeBnt—Abu—Sar
|                         |
MeLeu                     |
|                         |
D—Ala—Ala—MeAla—Val—MeLeu

9

According to the scheme, N-methyl-L-alanine is N-protected as its Boc (t-butyloxycarbonyl) derivative, then coupled with L-alanine benzyl ester p-tosylate salt, in the presence of bis-(2-oxo-3-oxazolidinyl)phosphinic chloride (BOP-Cl) as the peptide coupling reagent, to afford, after removal of the N-protection by trifluoroacetolysis, the O-protected dipeptide 1. Similarly, dipeptide 1 is then coupled with Boc-L-valine, N-deprotected, the derived tripeptide 2 coupled with Boc-MeLeu and N-deprotected to give partially protected tetrapeptide 3. Tetrapeptide 3 is then coupled with the known dipeptide Boc-Abu-Sar-OH (4). [R. M. Wenger, Helv. Chim. Acta 67 (1984) 502] with BOP-Cl as the coupling reagent to afford, after N-deprotection with trifluoroacetic acid, the hexapeptide 5.

Heptapeptide 6 is then formed by first coupling with N,O-isopropylidene-MeBMT in the presence of N-hydroxybenzotriazole and 1,3-dicyclohexylcarbodiimide, and subsequent removal of the isopropylidene acetal group by treatment with an acid, for example, HCl in methanol. The protected linear undecapeptide 7 is prepared by condensation of 6 with the known Boc-D-Ala-MeLeu-MeLeu-MeValOH tetrapeptide [R.M. Wenger, Helv. Chim. Acta. 66 (1983) 2672] in the presence of benzotriazol-1-yloxytris(dimethylamino)phosphonium hexafluorophosphate (BOP reagent). O-deprotection is achieved by treatment with aqueous NaOH in ethanol and N-deprotection by treatment with trifluoroacetic acid. The linear unprotected undecapeptide 8 is then cyclized at high dilution in the presence of a peptide coupling reagent, such as 1-propanephosphonic acid cyclic anhydride in the presence of 4-dimethylaminopyridine, to afford MeAla⁶-cyclosporin A (9).

The dihydro MeBmt derivatives of the cyclosporin analogs of the present invention are prepared by hydrogenation in an alcohol, such as methanol or ethanol, in the presence of a catalyst, such as, 10% palladium-on-charcoal.

The compounds described herein are also capable of enhancing the sensitivity of multidrug-resistant cells and, given their lack of nephrotoxicity, as measured in an in vivo mouse model, are expected to find broader clinical application than cyclosporin itself.

This invention relates to a method of sensitizing multidrug-resistant tumor cells to antitumor chemotherapeutic agents. It also relates to a method of increasing the sensitivity of drug-susceptible tumor cells to antitumor chemotherapeutic agents. In addition, this invention relates to a method of preventing the emergence of MDR tumor cells during a course of treatment with antitumor chemotherapeutic agents. Finally, this invention relates to a method of reducing the effective dosage of an antitumor chemotherapeutic agent during a course of treatment. It has been found that the compounds of formula I, wherein the 6-position is either MeAla or MeAbu, have the activity of increasing the sensitivity of multidrug-resistant mammalian cells in culture. It has also been found that the same compounds increase the sensitivity of drug-susceptible mammalian cells in culture.

Cyclosporin A (CsA), a member of the family of immunosuppressive cyclosporins, is the drug of choice for preventing organ transplant rejection, and is also beneficial in treating autoimmune diseases, such as type 1 diabetes, multiple sclerosis, uveitis and rheumatoid arthritis. Despite these advantages, broader clinical application of CsA has been hampered by its severe nephrotoxicity (as well as other major organ toxicity) within the standard dose range of between 5 mg and 20 mg per kilogram per day. CsA has also been shown to have the ability to reverse the resistance of tumor cells to certain antitumor chemotherapeutic agents, both in vitro and in vivo [Slater, L. et al., Proc. Am. Assoc. Cancer Res. 27, 392 (1982)].

Cytotoxic drugs are commonly used as antitumor chemotherapeutic agents. These agents are also called antiproliferative agents. The desired effect of cytotoxic drugs is selective cell death with destruction of the malignant neoplastic cells and relative sparing of normal cells.

Cytotoxic drugs have also proved valuable in the treatment of other non-neoplastic disorders including connective tissue or autoimmune diseases, metabolic disorders, dermatologic diseases, and DNA virus infections.

Proper use of cytotoxic drugs requires a thorough familiarity with the natural history and pathophysiology of the disease before selecting the cytotoxic agent, determining a dose, and undertaking therapy. Each patient must be carefully evaluated, with attention directed toward factors which may potentiate toxicity, such as overt or occult infections, bleeding dyscrasias, poor nutritional status, and severe metabolic disturbances. In addition, the functional condition of certain major organs, such as the liver, kidneys and bone marrow, is extremely important. Therefore, the selection of the appropriate cytotoxic agent and devising an effective therapeutic regimen is influenced by the presentation of the patient.

Cytotoxic drugs as antitumor chemotherapeutic agents can be subdivided into several broad categories, including; i) alkylating agents such as mechlorethamine, cyclophosphamide, melphalan, uracil mustard, chlorambucil, busulfan, carmustine, lomustine, semustine, streptozotocin, and decarbazine; ii) antimetabolites such as methotrexate, fluorouracil, fluorodeoxyuridine, cytarabine, azarabine, idoxuridine, mercaptopurine, azathioprine, thioguanine, and adenine arabinoside; iii) natural product derivatives such as vinblastine, vincristine, dactinomycin, daunorubicin, doxorubicin, mithramycin, bleomycin, etoposide, teniposide, and mitomycin-C and; iv) miscellaneous agents such as hydroxyurea, procarbezine, mitotane, and cis-platinum.

Important antitumor chemotherapeutic agents (with the usual effective dosage) to which clinical multidrug-resistance has been observed include vinblastine (0.1 mg per kilogram per week), vincristine (0.01 mg per kilogram per week), etoposide (35 to 50 mg per square meter per day), dactinomycin (0.15 mg per kilogram per day), doxorubicin (500 to 600 mg per square meter), daunorubicin (60 to 75 mg per square meter per week), and mithramycin (0.025 mg per kilogram per day). Multidrug-resistance has been shown to occur in vitro as well as in the clinic.

Multidrug-resistant cells lines are easily obtainable for in vitro determination of drug sensitization by compounds of the present invention, as well as other compounds with similar activity. These cell lines include NIH-OVCAR-3 (ATCC HTB161)., which is commercially available. Other cell lines can be readily developed in accordance with the methods described by Twentyman et al., Br. J. Cancer, 54, 253 (1986). This procedure selects for multidrug-resistant cells by culturing the parental drug sensitive cell line in the continued presence of a cytotoxic drug, for example, doxorubicin.

Drug sensitive cells will perish while multidrug-resistant cells will survive and grow despite the presence of the drug. Eventually, a multidrug-resistant cell population emerges and can be used in an assay system for the detection of agents which can modify the multidrug-resistance. Many cell lines are suitable as parental cell lines from which multidrug-resistant cells can be selected. These cell lines can be derived from humans or other mammals and can be derived from normal tissue or tumor tissue. Commercially available human cell lines derived from human tumor tissue include KB (ATCC CCL 17), NCI-H69 (ATCC HTB 119), CCRF-CCM (ATTC CCL 119), and K-562 (ATCC CCL 243). Other suitable, commercially available mammalian cells lines include LM(TK-) (ATCC CLL 1.3), and CHO-K1 (ATCC CCL 61).

The sensitivity of drug resistant cell lines can be compared with the parental cell line by assaying inhibition of cell growth during continuous exposure to the drug. Growth of the parental cells will be inhibited while the growth of resistant cells will not be inhibited. Cell growth can be measured by cell counting using an electronic cell counter, for example, COULTER COUNTER (COULTER ELECTRONICS, Herts England), and following the manufacturers recommended instructions for use. The COULTER COUNTER determines particle number and size distribution by impedence volume measurement. Cells may also be counted microscopically using a hemocytometer, but the electronic cell counter is preferred.

Cell growth can be measured by other techniques including cell staining. Cells can be stained by various agents including crystal violet, coomassie blue and methylene blue with methlene blue the preferred stain. Determining cell growth by methylene blue staining can be done as follows.

Equal numbers of cells of an anchorage dependent mammalian cell line are seeded in growth medium (e.g. alpha MEM plus 10% FBS) into a suitable culture vessel, e.g. plastic 96 well tissue culture plates. A cytotoxic drug (e.g. doxorubicin) is added to the cells in the dishes at various concentrations ranging between 0 and 100 uM. Following about 72 hours of continuous exposure to the cytotoxic agent, the growth medium is decanted and the cells are washed with a suitable buffer, e.g. phosphate buffered saline (PBS). About 2 ml of a solution of 2% methylene blue (dissolve methylene blue in a solution of about 50% ethanol in water) is added to the cells on the dishes. The dye is allowed to contact the cells for about 2 minutes. Excess dye is washed away with cold water and the plates are air dried. The dye stained cells are then solubilized by adding an equal volume to all wells of a solution of a detergent, e.g. 1% N-lauroyl-sarcosine. The amount of dye remaining in the wells directly correlates witht he number of cells in the well. The amount of methylene blue dye in the wells can be measured spectrophotometrically by measuring absorbance at 600 nm using an electronic ELISA plate spectrophotmeter (Minireader II, Dynatech Laboratories, Alexandria, VA). The typical results show decreased absorbance at 600 nm with increasing cytotoxic drug concentration indicating increased cell death with increased drug concentration.

Cell growth measured by either the cell counting method or the cell staining method should closely correlate. The staining method is preferable because of its simplicity and it is easily adaptable to automation which allows many experiments to be performed with many test compounds non-labor intensively.

Using the methylene blue cell staining method to measure cell growth, it has been found that the compounds of Formula I, wherein the 6-position is either MeAla or MeAbu can drug-sensitize multidrug-resistant mammalian cells in culture. It has also been found, using the same procedure, that the compounds of Formula I wherein the 6-position is either MeAla or MeAbu, can increase the drug sensitivity of the parental drug-sensitive mammalian cell line.

Chinese hamster ovary (CHO) derived cells were used as the parental cell line from which multidrug-resistant cells were selected as previously described. The cells were cultured in the presence of the cytotoxic agent doxorubicin with and without 1 ug/ml of a compound of Formula I wherein the 6-position is MeAla or MeAbu. The results are shown in Table 1:

TABLE 1

| Treatment | $IC_{50}$* Doxorubicin (uM) | |
|---|---|---|
| | Parental CHO cells (Drug Sensitive) | MDR CHO cells (multidrug-resistant) |
| Doxorubicin only | 0.17 ± 0.01 | 11.30 ± 0.51 |
| Doxorubicin plus 1 ug/ml 6-MeAla | 0.02 ± 0.00 | 0.64 ± 0.00 |

*$IC_{50}$ is defined as the doxorubicin concentration required to reduce cell growth, as measured by the methylene blue staining method, by 50% compared to cell growth in the absence of doxorubicin.

For the multidrug-resistant cells, the doxorubicin $IC_{50}$ was significantly reduced demonstrating the ability of the 6-position substituted cyclosporin analogs to sensitize multidrug-resistant cells to cytotoxic agents. Furthermore, for the drug-sensitive parental cells, the doxorubicin $IC_{50}$ was significantly reduced in the presence of the 6-position substituted cyclosporin analog.

The modulation of multidrug-resistance demonstrated by the 6-position substituted cyclosporin analogs described herein provides a method for treatment of multidrug-resistant tumors. The multidrug-resistance modulatory properties of the compounds described herein also provide a method for the prevention of the emergence of multidrug-resistant tumors during the course of cancer treatment. In addition, the 6-position substituted cyclosporin analogs described herein provide a method for increasing the sensitivity of drug-susceptible cells, to an antitumor chemotherapeutic agent. These same compounds additionally provide a method for reducing the required dosage of an antitumor chemotherapeutic agent.

The compounds described herein possess the multidrug-resistance modulatory properties of cyclosporin A without its immunosuppressive activity or nephrotoxicity. Therefore, the compounds of the present invention can be used in combination with cyclosporin A for the purpose of alleviating the potentially harmful side effects of cyclosporin A treatment.

All of the methods of this invention involve (1) the administration of a compound of formula I wherein the 6-position is either MeAla or MeAbu, prior to, together with or subsequent to the administration of an antitumor chemotherapeutic agent; (2) the administration of both compounds of formula I wherein the 6-position is either MeAla or MeAbu, prior to, together with or subsequent to the administration of an antitumor chemotherapeutic agent; (3) the administration of a combination of one or both compounds of formula I wherein the 6-position is either MeAla or MeAbu, and an antitumor chemotherapeutic agent, or (4) the administration of a combination of one or both compounds of formula I wherein the 6-position is either MeAla or MeAbu, an antitumor chemotherapeutic agent, and cyclosporin A.

For the treatment of multidrug-resistant tumor cells or tumor cells in general, one compound or both compounds of formula I wherein the 6-position is MeAla or MeAbu, either separately or in combination with an antitumor chemotherapeutic agent, may be administered orally, topically or parenterally in dosage unit formulations containing conventional non-toxic pharmaceutically acceptable carriers, adjuvants, adjuvants and vehicles. The term parenteral as used herein includes subcutaneous injections, intravenous, intramuscular, intrasternal injection or infusion techniques.

The pharmaceutical compositions containing the active ingredient(s) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay intestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be
(1) suspending agents such as sodium carboxymethylcellulose, methylcellulose, hydroxypropylmethylcellulose, sodium alginate, polyvinylpyrrolidone, gum tragacanth and gum acacia;
(2) dispersing or wetting agents which may be
   (a) a naturally-occurring phosphatide such as lecithin,
   (b) a condensation product of an alkylene oxide with a fatty acid, for example, polyoxyethylene stearate,
   (c) a condensation product of ethylene oxide with a long chain aliphatic alcohol, for example, heptadecaethylenoxycetanol,
   (d) a condensation product of ethylene oxide with a partial ester derived from a fatty acid and a hexitol such as polyoxyethylene sorbitol monooleate, or
   (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the immunoregulants are employed.

Dosage levels of the compounds of the present invention, of the order from about 0.5 mg to about 100 mg per kilogram body weight per day, with a preferred dosage range between about 20 mg to about 50 mg per kilogram body weight per day, are useful in the treatment of the above-indicated conditions (from about 25 mg to about 5 gms. per patient per day).

The amount of active ingredient that may be combined with the carrier materials to produce a single dosage form will vary depending upon the host treated and the particular mode of administration.

For example, a formulation intended for the oral administration of humans may contain 5 mg to 1 g of an active compound with an appropriate and convenient amount of carrier material which may vary from about 5 to about 95 percent of the total composition. Dosage unit forms will generally contain between from about 5 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate the present invention without limiting the same thereto.

EXAMPLE 1

The following example illustrates the processes for making an active compound to be used in the present invention.

Cyclo[-((2S,3R,4R,6E)-3-hydroxy-4-methyl-2-methylamino-6-octenoyl)-L-2-aminobutyryl-sarcosyl-N-methyl-L-leucyl-valyl-N-methyl-L-leucyl-L-alanyl-D-alanyl-N-methyl-L-leucyl-N-methyl-L-leucyl-N-methyl-L-valyl]

Step 1: Boc-N-Methyl-L-Alanyl-L-Alanine Benzyl Ester

A stirred solution of 13.41 h (0.666 mole) of Boc-N-methyl-L-alanine and 21.08 g (0.060 mole) of L-alanine benzyl ester tosylate in 350 ml of dry dichloromethane was cooled at $-5°$ C. 32.03 g (0.317 mole) of dry triethylamine was added, followed by 25.2 g (0.999 mole) of N-N-bis(2-oxo-3-oxazolidinyl)phosphinic chloride (BOP-Cl). The reaction was stirred at $-5°$ C. for 24 hours, then washed successively with 125 ml of 10% potassium bisulfate and 2×100 ml layer was dried over magnesium sulfate and concentrated to a small volume. The crude product was passed through a column of silica gel MERCK#7734 using 1:1 ether/hexane as the eluent, giving 17.1 g (78% of theory) of the blocked dipeptide. Fast Atom bombardment mass spectroscopy (FAB m.s.) showed a molecular ion peak at 365.

Step 2: N-Methyl-L-Alanyl-L-Alanine Benzyl Ester

To a stirred solution of 17 g (0.0466 mole) of Boc-N-methyl-L-alanyl-L-alanine benzyl ester in 150 ml of dry dichloromethane, cooled at $-10°$ C., was added 100 ml trifluoroacetic acid, which was previously cooled at $-10°$ C. The reaction mixture was stirred for 16 hours at $-5°$ C., then poured carefully with good stirring into a mixture of 177 g of sodium bicarbonate, ice, and 150 ml of dichloromethane. The organic layer was separated and the aqueous layer was further extracted with another 60 ml of dichloromethane. The combined organic layers were washed with 3×50 ml of saturated sodium bicarbonate solution, dried over magnesium sulfate, and evaporated to give 11.6 g (91% of theory) of crude product which was used in step 3 without further purification.

Step 3: Boc-L-Valyl-N-Methyl-L-Alanyl-L-Alanine Benzyl Ester

A mixture of 10.75 g (0.0407 mole) of N-methyl-L-alanyl-L-alanine benzyl ester and 9.73 g (0.0448 mole) of Boc-L-valine in 200 ml of dry dichloromethane was stirred and cooled at $-10°$ C. as 9.97 g (0.0986 mole) of triethylamine was added. After stirring for 15 minutes, 12.55 g (0.0493 mole) of BOP-Cl was added and the reaction was stirred at $-5°$ C. for 22 hours. The reaction was diluted with 100 ml of dichloromethane, washed with 100 ml of 10% potassium bisulfate, washed with 2×75 ml of saturated sodium bicarbonate solution, dried over magnesium sulfate, concentrated, and chromatographed on silica gel using 1:1 ether/hexane as the eluent. The product weighed 17.1 g (91% of theory). Its 200 MHz NMR spectrum in chloroform-d was consistent with the proposed structure.

Step 4: L-Valyl-N-Methyl-L-Alanyl-L-Alanine Benzyl Ester

A stirred solution of 17 g (0.0367 mole) Boc-L-valyl-N-methyl-L-alanyl-L-alanine benzyl ester in 170 ml of dry dichloromethane was cooled at $-10°$ C. as 85 ml of trifluoroacetic acid, previously cooled at $-15°$ C., was added. After 16 hours at $-5°$ C., the reaction was carefully poured with good stirring into a mixture of 93 g of sodium bicarbonate, ice, and 250 ml of dichloromethane. The organic layer was separated and the aqueous layer was extracted with another 75 ml of dichloromethane. The combined organic layers were washed with 3×75 ml of saturated sodium bicarbonate solution, dried over magnesium sulfate, and evaporated to give 12.8 g (96% of theory) of crude product which was used in step 5 without further purification. FAB m.s. showed a molecular ion peak at 364.

Step 5: Boc-N-Methyl-L-Leucyl-L-Valyl-N-Methyl-L-Alanyl-L-Alanine Benzyl Ester A solution of 13.17 g (0.0537 mole) of Boc-N-methyl-L-leucine in 370 ml of dry dichloromethane was stirred and cooled at 0° C. as one-half of 13.15 g. (0.130 mole) of dry triethylamine was added, followed by 15.05 g (0.0591 mole) of BOP-Cl. This was stirred at 0° C. for 3 hours. The remainder of the triethylamine was added, followed by a solution of 13 g (0.0358 mole) of L-valyl-N-methyl-L-alanyl-L-alanine benzyl ester in 50 ml of dry dichloromethane. The reaction was stirred at ice temperature for 22 hours, then washed with 125 ml of a 10% solution of potassium bisulfate. The organic layer was further washed with 2×100 ml of saturated sodium bicarbonate solution, dried over magnesium sulfate, concentrated to a small volume, and chromatographed on silica gel eluting with 1:1 ether/hexane gradually increasing the ether to 2:1. The product weighed 15.8 g (75% of theory), and the FAB m.s. showed a molecular ion peak at 591.

Step 6: N-Methyl-L-Leucyl-L-Valyl-N-Methyl-L-Alanyl-L-Alanine Benzyl Ester

A solution of 15.7 g (0.0266 mole) of Boc-N-methyl-L-leucyl-L-valyl-N-methyl-L-alanyl-L-alanine benzyl ester in 125 ml of dry dichloromethane was stirred and cooled to $-10°$ C. while 70 ml trifluoroacetic acid, previously cooled at $-15°$ C., was added. After 2 hours, the reaction was carefully added with good stirring to a mixture of 105 g of sodium bicarbonate, ice, and 200 ml of dichloromethane. The organic layer was separated and the aqueous layer was extracted with another 50 ml of dichloromethane. The combined organic layers were washed with 3×80 ml of saturated sodium bicarbonate solution, dried over magnesium sulfate, and evaporated leaving 11.85 g (91% of theory) of product. The FAB m.s. showed a molecular ion peak at 491.

Step 7: Boc-L-2-Aminobutyryl-Sarcosyl-N-Methyl-L-Leucyl-L-Valyl-N-Methyl-L-Alanyl-L-Alanine Benzyl Ester A solution of 11.7 g (0.0238 mole) of N-methyl-L-leucyl-L-valyl-N-methyl-L-alanyl-L-alanine benzyl ester and 7.19 g (0.0262 mole) of Boc-L-2-aminobutyryl-sarcosine [R. M. Wenger, *Helv. Chim Acta* 67 (1984) 502] in 400 ml of dry dichloromethane was stirred and cooled at $-10°$ C., as 6.41 g (0.0634 mole) of dry triethylamine was added, followed by 7.33 g (0.0288 mole) of BOP-Cl. After stirring for 72 hours, the reaction was washed with 3×100 ml of saturated sodium bicarbonate solution. The organic layer was dried over magnesium sulfate, evaporated, and chromatographed on silica gel using 1:1 ether/ethyl acetate as the eluent. The product weighted 9.1 g (51% of theory) and the FAB m.s. showed a molecular ion peak at 747.

Step 8:
L-2-Aminobutyryl-Sarcosyl-N-Methyl-L-Leucyl-L-Valyl-N-Methyl-L-Alanyl-L-Alanine Benzyl Ester A solution of 9.0 g (0.0120 mole) of Boc-L-2-aminobutyryl-sarcosyl-N-methyl-L-leucyl-L-valyl-N-methyl-L-alanyl-L-alanine benzyl ester in 90 ml of dry dichloromethane was stirred and cooled at −10° C. as 60 ml of trifluoroacetic acid, previously cooled at −10° C., was added. After 16 hours, the reaction was carefully poured into a mixture of 90 g of sodium bicarbonate, ice, and 100 ml of dichloromethane. The organic layer was separated and the aqueous layer was extracted with 75 ml of dichloromethane. The combined organic layers were washed with 3×75 ml of saturated sodium bicarbonate solution, dried over magnesium sulfate, and evaporated. The crude product weighed 7.0 g (90% of theory), and was used in step 9 without further purification. The FAB m.s. showed a molecular ion peak at 647.

Step 9: ((4S,5R,1′R,3′E)-2,2,3-Trimethyl-5-(1′-methyl-3′-pentenyl)-4-oxazolidinecarbonyl)-L-2-amino-butyryl-sarcosyl-N-methyl-L-leucyl-L-valyl-N-methyl-L-alanyl-L-alanine benzyl ester To a mixture of (4S,5R,1′R,3′E)-2,2,3-trimethyl-5-(1′-methyl-3′-pentenyl)-4-oxazolidinecarboxylic acid (prepared by heating at reflux temperature a solution of (2S, 3R, 4R, 6E)-3-hydroxy -4-methyl-2-methylamino-6-octenoic acid [prepared by the process set forth in R. M. Wenger, *Helv. Chim. Acta*, 66 (1983) 2308] (250 mg., 1.24 mmol.) in dry acetone (80 ml) for 24 hours and subsequent evaporation under diminished pressure) in 1 ml acetone were added, successively with stirring under a nitrogen atmosphere, dry tetrahydrofuran (10 ml), N-methylmorpholine (152 ml, 1.40 mmol.), N-hydroxybenzotriazole (335.7 mg., 2.48 mmol.), and L-2-aminobutyryl-sarcosyl-N-methyl-L-leucyl-valyl-N-methyl-L-alanyl-L-alanine benzyl ester (803 mg., 1.24 mmol.). The reaction mixture was cooled in an ice bath and 1,3-dicyclohexylcarbodiimide (267.8 mg., 1.30 mmol) added. The mixture was allowed to attain room temperature, and stirring was continued for an additional 24 hours. The mixture was diluted with dichloromethane (60 ml) and washed with saturated sodium hydrogencarbonate solution (30 ml). The aqueous layer was extracted with dichloromethane (30 ml), and the combined organic extracts were dried (sodium sulfate) and evaporated. The residue was triturated with diethyl ether, filtered, and evaporated. The resulting crude material was applied to a column of silica gel (MERCK #7734, packed as a slurry in 2% methanol in dichloromethane). Elution was effected with 2% methanol in dichloromethane. Fractions containing pure product were combined and evaporated to afford the protected N,O-isopropylidene-MeBmt-Abu-Sar-MeLeu-Val-MeAla-AlaOBzl heptapeptide as a thick syrup; yield 629 mg. (58%). Its 200 MHz NMR spectrum in chloroform-d was in accord with the desired structure.

Step 10:
((2S,3R,4R,6E-)-3-Hydroxy-4-methyl-2-methylamino-6-octenoyl)-L-2-aminobutyryl-sarcosyl-N-methyl-L-leucyl-L-valyl-N-methyl-L-alanyl-L-alanine benzyl ester To a solution of N,O-isopropylidene-MeBmt-Abu-Sar-MeLeu-Val-MeAla-Ala-OBzl (620 mg., 0.71 mmol) in methanol (8 ml) was added with stirring 1N hydrochloric acid (0.70 ml). The reaction mixture was stirred for 18 hours at room temperature, then neutralized with solid sodium hydrogencarbonate (410 mg). The mixture was filtered, the filter washed with methanol, and the combined filtrate and washings evaporated. The crude material was taken up in dichloromethane and filtered. The resulting syrup was dissolved in a small volume of dichloromethane, and the solution was applied to a column of silica gel (MERCK #7734, packed as a slurry in 4% methanol in dichloromethane). Elution was effected with 4% methanol in dichloromethane. Fractions containing slower-moving product were combined and evaporated to give the partially protected H-MeBmt-Abu-Sar-MeLeu-Val-MeAla-AlaOBzl heptapeptide as a thick syrup; yield 368 mg (61%).

Step 11:
Boc-D-Alanyl-N-methyl-L-leucyl-N-methyl-L-leucyl-N-methyl-L-valyl-((2S,3R,4R,6E-)-3-hydroxy-4-methyl-2-methylamino-6-octenoyl)-L-2-aminobutyryl-sarcosyl-N-methyl-L-leucyl-L-valyl-N-methyl-L-alanyl-L-alanine benzyl ester To a solution of Boc-D-Ala-MeLeu-MeLeu-MeValOH [prepared by the process set forth in R. M. Wenger, *Helv. Chim. Acta*, 66 (1983) 2672] (246 mg, 0.442 mmol) and H-MeBmt-Abu-Sar-MeLeu-Val-MeAla-AlaOBzl (368 mg., 0.443 mmol) in dry dichloromethane (11 ml) were added N-methylmorpholine (48.7 ml, 0.443 mmol) and benzotriazol-1-yloxytris(dimethylamino) phosphonium hexafluorophosphate (196 mg, 0.443 mmol). The reaction mixture was stirred 5 days at room temperature under a nitrogen atmosphere. It was then diluted with dichloromethane (100 ml), washed with water (50 ml), dried (sodium sulfate) and evaporated. The crude product was chromatographed on a column of silica gel (MERCK #7734, packed as a slurry in 4% methanol in dichloromethane). Elution was effected with 4% methanol in dichloromethane. Fractions containing pure product were combined and evaporated to give the desired Boc-D-Ala-MeLeu-MeLeu-MeVal-MeBmt-Abu-Sar-MeLeu-Val-MeAla-AlaOBzl undecapeptide; yield 349.8 mg. (57.6%).

Step 12:
Boc-D-Alanyl-N-methyl-L-leucyl-N-methyl-L-leucyl-N-methyl-L-valyl-((2S,3R,4R,6E-)-3-hydroxy-4-methyl-2-methylamino-6-octenoyl)-L-2-aminobutyryl-sarcosyl-N-methyl-L-leucyl-L-valyl-N-methyl-L-alanyl-L-alanine To a solution Boc-D-Ala-MeLeu-MeLeu-MeVal-MeBmt-Abu-Sar-MeLeu-Val-MeAla-AlaOBzl (330 mg., 0.241 mmol) in ethanol (10 ml) cooled to ice temperature was added 0.2N aqueous sodium hydroxide (1.2 ml). The reaction mixture was kept at 5° C. for 24 hours, brought to pH 5 with several drops of glacial acetic acid and then evaporated under diminished pressure. The residue was taken up in dichloromethane (30 ml) and washed with water (15 ml). The aqueous layer was extracted with dichloromethane (15 ml), and the combined organic extracts were dried (sodium sulfate) and evaporated. The resulting material was applied to a column of silica gel (Merck #7734, packed as a slurry in 4% methanol in dichloromethane). Elution initially with 4% methanol in dichloromethane gave unreacted starting material and benzyl alcohol; subsequent elution with 15% methanol in dichloromethane afforded the partially protected Boc-D-Ala-MeLeu-MeLeu-MeVal-MeBmt-Abu-Sar-MeLeu-Val-MeAla-AlaOH undecapeptide; yield 239 mg. (77.5%).

Step 13:
D-Alanyl-N-methyl-L-leucyl-N-methyl-L-leucyl-N-methyl-L-valyl-(2S,3R,4R,6E-)-3-hydroxy-4-methyl-2-methylamino-6-octenoyl)-L-2-aminobutyryl-sarcosyl-N-methyl-L-leucyl-L-valyl-N-methyl-L-alanyl-L-alanine Boc-D-Ala-MeLeu-MeLeu-MeVal-MeBmt-Abu-Sar-MeLeu-Val-MeAla-AlaOH (239 mg., 0.187 mmol) was cooled to $-15°$ C. and treated with precooled trifluoroacetic acid (3 ml) for 1 hour at $-15°$ C. The reaction mixture was then evaporated under diminished pressure (bath temperature of $0°$ C.) and coevaporated several times with dichloromethane. The crude material was taken up in dichloromethane (30 ml) and washed with saturated sodium hydrogencarbonate solution (15 ml). The organic layer was dried (sodium sulfate) and evaporated. The product was triturated with diethyl ether and the resulting amorphous solid was filtered, washed with ether and dried in vacuo; yield 195 mg. (88.6%).

Step 14:
Cyclo[-((2S,3R,4R,6E)-3-Hydroxy-4-methyl-2-methylamino-6-octenoyl)-L-2-aminobutyryl-sarcosyl-N-methyl-L-leucyl-Valyl-N-methyl-L-alanyl-L-alanyl-D-alanyl-N-methyl-L-leucyl-N-methyl-L-leucyl-N-methyl-L-valyl]

To a solution of H-D-Ala-MeLeu-MeLeu-MeVal-MeBmt-Abu-Sar-MeLeu-Val-MeAla-AlaOH (195 mg., 0.165 mmol) in dichloromethane (650 ml) were added 4-dimethylaminopyridine (97 mg., 0.794 mmol) followed by 1-propanephosphonic acid cyclic anhydride (50 wt. % solution in dichloromethane) (0.2 ml). The reaction mixture was stirred at room temperature for 24 hours, concentrated down to 50 ml and washed with saturated sodium hydrogencarbonate solution. The organic layer was dried (sodium sulfate) and evaporated. The crude material was applied to a column of silica gel (MERCK #7734, packed as a slurry in 3:1 hexane-acetone). Elution was effected initially with 3:1 hexane-acetone and subsequently with 2:1 hexane-acetone. Fractions containing pure product were combined and evaporated to give MeAla$^6$-CsA as a white amorphous solid; yield 121 mg. (63%). Its 400 MHz NMR spectrum in chloroform-d was in accord with the desired structure. FAB m.s. showed a molecular ion at m/z 1160.

What is claimed is:

1. A method of treatment for increasing the sensitivity of tumor cells to anti-cancer chemotherapeutic agents, said tumor cells being susceptible to anticancer chemotherapeutic agents, and said tumor cells having become resistant to chemotherapy comprising:
administration to a mammalian species in need of such treatment a therapeutically effective amount of a compound of formula I

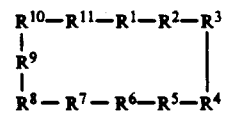

wherein:
$R^1$ is MeBmt;
$R^2$ Abu;
$R^3$ is Sar;
$R^4$, $R^9$ and $R^{10}$ are MeLeu;
$R^5$ is Val;
$R^6$ is MeAla or MeAbu;
$R^7$ is Ala;
$R^8$ is D-Ala; and
$R^{11}$ is MeVal, and a nontoxic pharmaceutical carrier.

2. A method of treatment for increasing the sensitivity of tumor cells to anti-cancer chemotherapeutic agents according to claim 1, comprising: administration to a mammalian species in need of such treatment a therapeutically effective amount of a compound of formula I

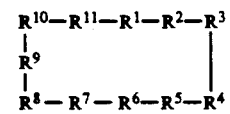

wherein:
$R^1$ is MeBmt;
$R^2$ is Abu;
$R^3$ is Sar;
$R^4$, $R^9$ and $R^{10}$ are MeLeu;
$R^5$ is Val;
$R^6$ is MeAla;
$R^7$ is Ala;
$R^8$ is D-Ala; and
$R^{11}$ is MeVal.

3. A method of treatment for increasing the sensitivity of tumor cells to anti-cancer chemotherapeutic agents according to claim 1, comprising: administration to a mammalian species in need of such treatment a therapeutically effective amount of a compound of formula I

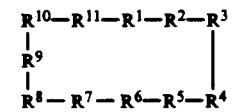

wherein:
$R^1$ is MeBmt;
$R^2$ is Abu;
$R^3$ is Sar;
$R^4$, $R^9$ and $R^{10}$ are Meleu;
$R^5$ is Val;
$R^6$ is MeAbu;
$R^7$ is Ala;
$R^8$ is D-Ala; and
$R^{11}$ is MeVal.

4. A method of treatment according to claim 1 comprising:
administration to a mammalian species in need of such treatment a therapeutically effective amount of active agent comprising a compound of formula I wherein $R^6$ is MeAla, and a compound of formula I wherein $R^6$ is MeAbu.

5. A method of treatment of tumor cells, said tumor cells being susceptible to anti-cancer chemotherapeutic agents, and said tumor cell having become resistant to chemotherapy comprising: administration to a mammalian species in need of such treatment, of a therapeutically effective amount of said anti-cancer chemotherapeutic agent, and an effective amount of a compound of formula I $$\begin{array}{c} R^{10}-R^{11}-R^1-R^2-R^3 \\ | \qquad \qquad \qquad | \\ R^9 \qquad \qquad \qquad | \\ | \qquad \qquad \qquad | \\ R^8-R^7-R^6-R^5-R^4 \end{array} \qquad I$$

wherein:
- $R^1$ is MeBmt;
- $R^2$ is Abu;
- $R^3$ is Sar;
- $R^4$, $R^9$ and $R^{10}$ are MeLeu;
- $R^5$ is Val;
- $R^6$ is MeAla or MeAbu;
- $R^7$ is Ala;
- $R^8$ is D-Ala; and
- $R^{11}$ is MeVal; and
- a non-toxic pharmaceutical carrier.

6. A method of treatment of tumor cells according to claim 5, comprising: administration to a mammalian species in need of such treatment a therapeutically effective amount of an anti-cancer chemotherapeutic agent selected from the group consisting of vincristine and daunorubicin, and an effective amount of a compound of formula I $$\begin{array}{c} R^{10}-R^{11}-R^1-R^2-R^3 \\ | \qquad \qquad \qquad | \\ R^9 \qquad \qquad \qquad | \\ | \qquad \qquad \qquad | \\ R^8-R^7-R^6-R^5-R^4 \end{array} \qquad I$$

wherein:
- $R^1$ is MeBmt;
- $R^2$ is Abu;
- $R^3$ is Sar;
- $R^4$, $R^9$ and $R^{10}$ are MeLeu;
- $R^5$ is Val;
- $R^6$ is MeAla or MeAbu;
- $R^7$ is Ala;
- $R^8$ is D-Ala; and
- $R^{11}$ is MeVal.

7. A pharmaceutical composition for increasing the sensitivity of tumor cells to anti-cancer chemotherapeutic agents, said tumors being susceptible to anti-cancer chemotherapeutic agents, and said tumor cells having become resistant to chemotherapy comprising a therapeutically effective amount of a compound of formula I $$\begin{array}{c} R^{10}-R^{11}-R^1-R^2-R^3 \\ | \qquad \qquad \qquad | \\ R^9 \qquad \qquad \qquad | \\ | \qquad \qquad \qquad | \\ R^8-R^7-R^6-R^5-R^4 \end{array} \qquad I$$

wherein:
- $R^1$ is MeBmt;
- $R^2$ is Abu;
- $R^3$ is Sar;
- $R^4$, $R^9$ and $R^{10}$ are MeLeu;
- $R^5$ is Val;
- $R^6$ is MeAla or MeAbu;
- $R^7$ is Ala;
- $R^8$ is D-Ala; and
- $R^{11}$ is MeVal; and
- a non-toxic pharmaceutical carrier.

8. A pharmaceutical composition for treatment of tumor cells, said tumor cells being susceptible to anti-cancer chemotherapeutic agents, and said tumor cells having become resistant to chemotheraphy comprising: a therapeutically effective amount of an anti-cancer chemotherapeutic agent selected form the group consisting of vincristine and daunorubicin, and an effective amount of a compound of formula I $$\begin{array}{c} R^{10}-R^{11}-R^1-R^2-R^3 \\ | \qquad \qquad \qquad | \\ R^9 \qquad \qquad \qquad | \\ | \qquad \qquad \qquad | \\ R^8-R^7-R^6-R^5-R^4 \end{array} \qquad I$$

wherein:
- $R^1$ is MeBmt;
- $R^2$ is Abu;
- $R^3$ is Sar;
- $R^4$, $R^9$ and $R^{10}$ are MeLeu;
- $R^5$ is Val;
- $R^6$ is MeAla or MeAbu;
- $R^7$ is Ala;
- $R^8$ is D-Ala; and
- $R^{11}$ is MeVal; and
- a non-toxic pharmaceutical carrier.

* * * * *